(12) United States Patent
Van Tol et al.

(10) Patent No.: US 11,684,387 B2
(45) Date of Patent: Jun. 27, 2023

(54) METHODS AND ULTRASONIC DEVICES AND SYSTEMS FOR VESSEL SEALING

(71) Applicant: Covidien LP, Mansfield, MA (US)

(72) Inventors: David J. Van Tol, Boulder, CO (US); Kelly E. Goodman, Boulder, CO (US); Keith W. Malang, Longmont, CO (US); Christopher T. Tschudy, Arvada, CO (US)

(73) Assignee: Covidien LP, Mansfield, MA (US)

( * ) Notice: Subject to any disclaimer, the term of this patent is extended or adjusted under 35 U.S.C. 154(b) by 444 days.

(21) Appl. No.: 17/034,443

(22) Filed: Sep. 28, 2020

(65) Prior Publication Data

US 2021/0153888 A1    May 27, 2021

Related U.S. Application Data

(60) Provisional application No. 62/939,763, filed on Nov. 25, 2019.

(51) Int. Cl.
*A61B 17/32*    (2006.01)
*A61B 17/00*    (2006.01)
*A61B 18/00*    (2006.01)

(52) U.S. Cl.
CPC .......... *A61B 17/320092* (2013.01); *A61B 2017/00026* (2013.01); *A61B 2017/320095* (2017.08);
(Continued)

(58) Field of Classification Search
CPC .. A61B 17/320092; A61B 2017/00026; A61B 2017/320095; A61B 2018/00648;
(Continued)

(56) References Cited

U.S. PATENT DOCUMENTS 4,646,754 A    3/1987 Seale
5,001,649 A    3/1991 Lo et al.
(Continued)

FOREIGN PATENT DOCUMENTS

AU    2019203019 B1    10/2019

OTHER PUBLICATIONS

U.S. Appl. No. 62/678,724, filed May 31, 2018 to Kelly E. Goodman.
(Continued)

*Primary Examiner* — George J Ulsh
(74) *Attorney, Agent, or Firm* — Carter, DeLuca & Farrell LLP

(57) ABSTRACT

A method for sealing a vessel includes supplying electrical energy to an ultrasonic surgical instrument having an end effector and a transducer coupled to the end effector, when the end effector is grasping a vessel, sensing parameters of the vessel when the end effector achieves a predetermined velocity, estimating a size of the vessel based on the sensed parameters, controlling the electrical energy based on maintaining a predetermined initial heating rate of heating the vessel until a predetermined amount of energy corresponding to the estimated size of the vessel has been delivered, and controlling the electrical energy based on a predetermined heating rate curve of heating the vessel after the predetermined amount of energy corresponding to the estimated size of the vessel has been delivered.

20 Claims, 5 Drawing Sheets

(52) U.S. Cl.
CPC ............... *A61B 2018/00648* (2013.01); *A61B 2018/00702* (2013.01)

(58) Field of Classification Search
CPC ........... A61B 2018/00702; A61B 2017/00084; A61B 2017/320094
See application file for complete search history.

(56) References Cited

U.S. PATENT DOCUMENTS

| | | |
|---|---|---|
| 5,185,585 A | 2/1993 | Newell et al. |
| 5,406,503 A | 4/1995 | Williams, Jr. et al. |
| 5,449,370 A | 9/1995 | Vaitekunas |
| 6,995,622 B2 | 2/2006 | Partridge et al. |
| 7,134,341 B2 | 11/2006 | Girmonsky et al. |
| 7,165,451 B1 | 1/2007 | Brooks et al. |
| 7,221,230 B2 | 5/2007 | Partridge et al. |
| 7,224,236 B2 | 5/2007 | Partridge et al. |
| RE40,709 E | 5/2009 | Akahane et al. |
| 8,061,014 B2 | 11/2011 | Smith et al. |
| 8,403,949 B2 | 3/2013 | Palmer et al. |
| 10,441,345 B2 | 10/2019 | Aldridge et al. |
| 2005/0020967 A1 | 1/2005 | Ono |
| 2005/0070800 A1 | 3/2005 | Takahashi |
| 2007/0016235 A1 | 1/2007 | Tanaka et al. |
| 2008/0015620 A1 | 1/2008 | Friedman et al. |
| 2009/0036913 A1 | 2/2009 | Wiener et al. |
| 2009/0036914 A1 | 2/2009 | Houser |
| 2009/0143804 A1 | 6/2009 | Palmer et al. |
| 2010/0292573 A1 | 11/2010 | Tanaka |
| 2011/0009890 A1 | 1/2011 | Palmer et al. |
| 2011/0082486 A1 | 4/2011 | Messerly et al. |
| 2011/0241786 A1 | 10/2011 | Gilbert |
| 2012/0078139 A1* | 3/2012 | Aldridge ............ A61B 18/1206 601/2 |
| 2012/0136279 A1 | 5/2012 | Tanaka et al. |
| 2013/0289591 A1 | 10/2013 | Boudreaux et al. |
| 2014/0276738 A1* | 9/2014 | Price .................. A61B 18/1445 606/33 |
| 2016/0374711 A1 | 12/2016 | Van Tol et al. |
| 2017/0296169 A1* | 10/2017 | Yates ................... A61B 17/105 |
| 2019/0365410 A1* | 12/2019 | Goodman ....... A61B 17/320092 |

OTHER PUBLICATIONS

Extended European Search Report issued in corresponding European Application No. 20208861.3 dated Apr. 22, 2021, 8 pages.

* cited by examiner

METHODS AND ULTRASONIC DEVICES AND SYSTEMS FOR VESSEL SEALING

CROSS REFERENCE TO RELATED APPLICATION

The present application claims the benefit of and priority to U.S. Provisional Application Ser. No. 62/939,763, filed on Nov. 25, 2019, the entire contents of which are incorporated herein by reference.

FIELD

The present disclosure relates to a method and an ultrasonic surgical device or system for sealing a vessel. More particularly, the present disclosure relates to a method and an ultrasonic surgical device or system that controls delivery of electrical energy to seal the vessel based on a size of the vessel.

BACKGROUND

Ultrasonic surgical devices are used for treating many medical conditions, such as removal of tissue and cauterization and sealing of vessels. Ultrasonic surgical devices utilize ultrasonic energy to generate vibrations with an ultrasonic transducer along a longitudinal axis of a cutting blade. Unlike electrosurgical devices, which require electrical current to flow through a patient, ultrasonic surgical devices operate by applying mechanical action of a transducer that is driven at a mechanical resonant frequency. By placing a resonant wave along the length of the blade, high-speed longitudinal mechanical movement is produced at the end of the blade. Ultrasonic surgical devices are advantageous because the mechanical vibrations transmitted to the end of the blade are effective at treating tissue using the heat energy produced by the mechanical movements. Ultrasonic surgical devices are particularly well suited for minimally invasive procedures, such as endoscopic or laparoscopic procedures, where the blade is passed through a trocar to reach the surgical site. Further, ultrasonic surgical devices have been demonstrated to achieve hemostasis and sealing of tissue with minimal lateral thermal damage and low smoke generation.

Since vessels differ in size, treating different vessels with a single treatment approach may not provide ideal results. Accordingly, there is continuing interest in improving treatment of vessels to account for the size of the target vessel.

SUMMARY

The present disclosure provides an ultrasonic surgical device and system for supplying energy to seal a vessel based on the size of the vessel, and a method for controlling the ultrasonic surgical device or system. In accordance with aspects of the present disclosure, controlling a heating rate of a vessel based on the size of the vessel, an ultrasonic surgical device is capable of more effectively sealing the vessel.

The present disclosure relates to controlling delivery of electrical energy to seal vessels based on vessel size. In accordance with embodiments of the present disclosure, a method for sealing a vessel includes supplying electrical energy to an ultrasonic surgical instrument having an end effector and a transducer coupled to the end effector, when the end effector is grasping a vessel, sensing parameters of the vessel when the end effector achieves a predetermined velocity, estimating a size of the vessel based on the sensed parameters, controlling the electrical energy based on maintaining a predetermined initial heating rate of heating the vessel until a predetermined amount of energy corresponding to the estimated size of the vessel has been delivered, and controlling the electrical energy based on a predetermined heating rate curve of heating the vessel after the predetermined amount of energy corresponding to the estimated size of the vessel has been delivered.

In an aspect, the predetermined heating rate curve decreases from the predetermined initial heating rate.

In another aspect, sensing parameters of the vessel includes sensing an impedance of the vessel.

In another aspect, controlling the electrical energy based on maintaining the predetermined initial heating rate of heating the vessel includes controlling the electrical energy based on maintaining the predetermined heating rate of heating the vessel until 20 joules of energy have been delivered, when the estimated size of the vessel is less than 5 millimeters.

In still another aspect, controlling the electrical energy based on maintaining the predetermined initial heating rate of heating the vessel includes controlling the electrical energy based on maintaining the predetermined initial heating rate of heating the vessel until 40 joules of energy have been delivered, when the estimated size of the vessel is greater than or equal to 5 millimeters.

In still another aspect, controlling the electrical energy based on the predetermined heating rate curve of heating the vessel includes halting the electrical energy after a predetermined duration of time.

In still another aspect, controlling the electrical energy based on maintaining the predetermined initial heating rate of heating the vessel includes detecting a rate of change of a resonant frequency of the transducer over time. Controlling the electrical energy based on maintaining the predetermined initial heating rate of heating the vessel includes controlling an amplitude of the electrical energy based on the detected rate of change of the resonant frequency over time.

In yet still another aspect, controlling the electrical energy based on the predetermined heating rate curve of heating the vessel includes detecting a rate of change of a resonant frequency of the transducer over time. Controlling the electrical energy based on the predetermined heating rate curve of heating the vessel includes controlling an amplitude of the electrical energy based on the detected rate of change of the resonant frequency over time.

In accordance with embodiments of the present disclosure, an ultrasonic surgical system includes a transducer, an end effector coupled to the transducer and configured to grasp and seal a vessel, a power source configured to supply electrical energy for the transducer, a sensor configured to sense parameters of the vessel, and a controller. The controller is configured to estimate a size of the vessel based on the sensed parameters, control the electrical energy based on maintaining a predetermined initial heating rate of heating the vessel until a predetermined amount of energy corresponding to the estimated size of the vessel has been delivered, and control the electrical energy based on a predetermined heating rate curve of heating the vessel after the predetermined amount of energy corresponding to the estimated size of the vessel has been delivered.

In an aspect, the predetermined heating rate curve decreases from the predetermined initial heating rate.

In another aspect, the sensed parameters include an impedance of the vessel.

In another aspect, the predetermined amount of energy is 20 joules when the estimated size of the vessel is less than 5 millimeters.

In still another aspect, the predetermined amount of energy is 40 joules when the estimated size of the vessel is greater than or equal to 5 millimeters.

In still another aspect, the controller is configured, in controlling the electrical energy based on the predetermined heating rate curve of heating the vessel, to halt the electrical energy after a predetermined duration of time.

In yet still another aspect, the controller is configured, in controlling the electrical energy based on maintaining the predetermined initial heating rate of heating the vessel, to detect a rate of change of a resonant frequency of the transducer over time. The controller is configured, in controlling the electrical energy based on maintaining the predetermined initial heating rate of heating the vessel, to control an amplitude of the electrical energy based on the detected rate of change of the resonant frequency over time.

In yet still another aspect, the controller is configured, in controlling the electrical energy based on the predetermined heating rate curve of heating the vessel, to detect a rate of change of a resonant frequency of the transducer over time, and to control an amplitude of the electrical energy based on the detected rate of change of the resonant frequency over time.

In accordance with embodiments of the present disclosure, a nontransitory storage medium storing instructions that, when executed by a processor, cause the processor to perform a method for sealing a vessel. The method includes supplying electrical energy to an ultrasonic surgical instrument having an end effector and a transducer coupled to the end effector, when the end effector is grasping a vessel, sensing parameters of the vessel when the end effector achieves a predetermined velocity, estimating a size of the vessel based on the sensed parameters, controlling the electrical energy based on maintaining a predetermined initial heating rate of heating the vessel until a predetermined amount of energy corresponding to the estimated size of the vessel has been delivered, and controlling the electrical energy based on a predetermined heating rate curve of heating the vessel after the predetermined amount of energy corresponding to the estimated size of the vessel has been delivered.

Further details and aspects of exemplary embodiments of the present disclosure are described in more detail below with reference to the appended figures.

BRIEF DESCRIPTION OF THE DRAWINGS

The present disclosure may be understood by reference to the accompanying drawings, when considered in conjunction with the subsequent, detailed description, in which.

DETAILED DESCRIPTION

Generally, the present disclosure provides an ultrasonic surgical device and system and a method for controlling a heating rate of a vessel based on the size of the vessel. In accordance with aspects of the present disclosure, the ultrasonic surgical device estimates a size of a vessel to be sealed. Based on the estimated size of the vessel, the ultrasonic surgical device controls a heating rate of the vessel to seal the vessel. An ultrasonic surgical device includes a transducer that provides and couples mechanical motion to an end effector. When the transducer is driven at a resonant frequency, the end effector achieves maximum motion for a particular input energy. Various factors can affect the resonant frequency of a transducer and cause it to drift or shift, including temperature. Thus, there is a relationship between temperature and the resonant frequency of an ultrasonic transducer. In accordance with aspects of the present disclosure, an ultrasonic surgical device can achieve an appropriate heating rate of a vessel by monitoring changes in the resonant frequency of the transducer over time and controlling the electrical energy supplied to the ultrasonic surgical device based on the changes in resonant frequency. By using these various controls, the ultrasonic surgical device provides controlled ultrasonic mechanical motions to seal various vessels in accordance with embodiments of the present disclosure.

Figure 1A:
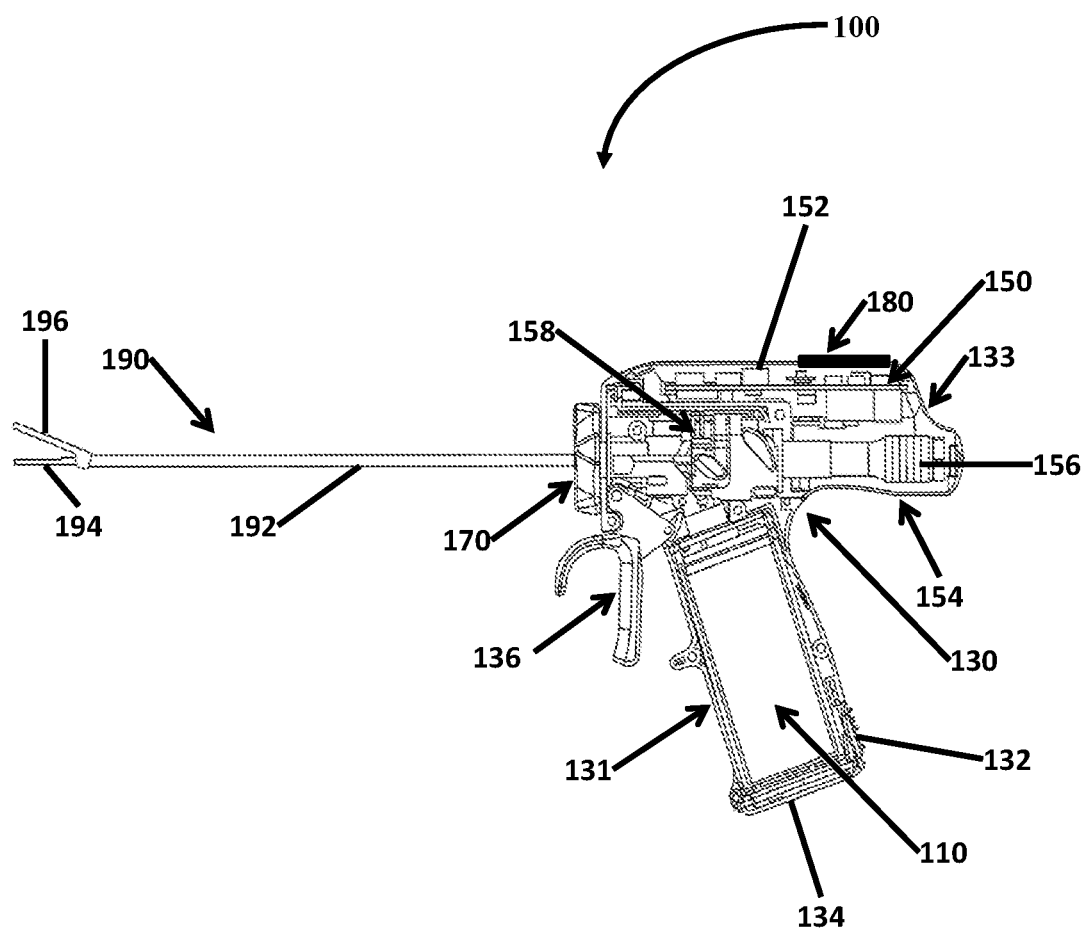
FIG. 1A is a side elevation view of an ultrasonic surgical device in accordance with embodiments of the present disclosure.
Figure 1B:
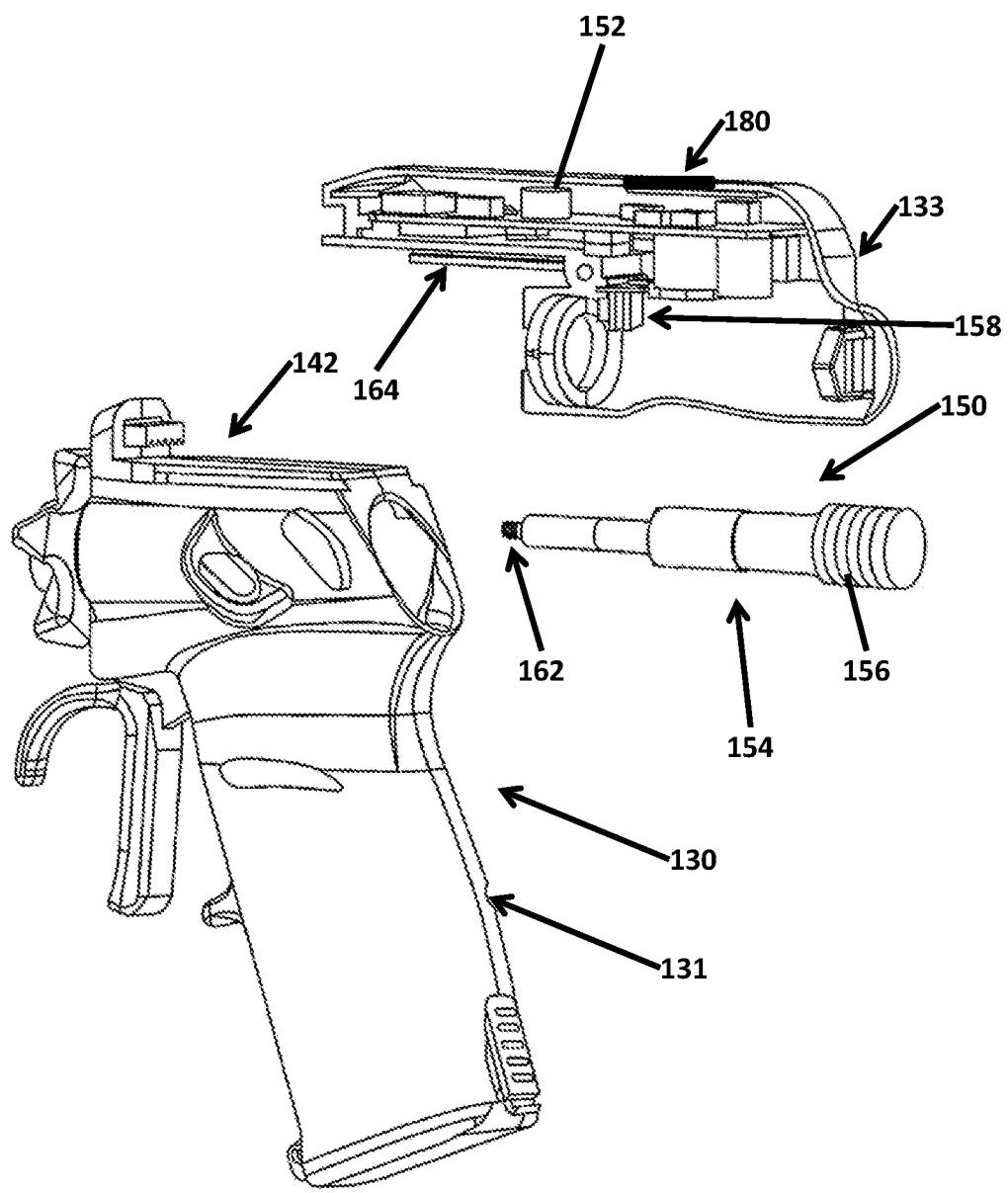
FIG. 1B is a perspective view of parts separated, which shows the left portion of a handle, a transducer, and the right portion of the ultrasonic surgical device of FIG. 1A in accordance with embodiments of the present disclosure.

With reference to FIGS. 1A and 1B, an ultrasonic surgical device 100 for treating tissue is illustrated. The ultrasonic surgical device 100 includes a power source 110, a housing 130, a transducer 150, and an ultrasonic probe 190. The power source 110 provides DC power to the transducer 150. In various embodiments, the power source 110 may be a portable power source, such as a battery, that can be carried to provide DC power at any place. In a further embodiment, the power source 110 may be insertable or integrated into the housing 130 so that the ultrasonic surgical device 100 may be portably carried without disturbances of any cable. In yet another embodiment, the power source 110 may be rechargeable so that the power source 110 may be reusable. In yet another embodiment, the power source 110 may receive power from a wall outlet.

In another embodiment, the power source 110 may include a converter that is connected to an alternating current (AC) power source and converts the AC power to DC power. The AC power source may be of a relatively low frequency, such as about 60 hertz (Hz), while the ultrasonic surgical device 100 operates at a higher frequency. Thus, the power source 110 may convert the low frequency AC power to DC power so that the DC power may then be inverted to AC power having a frequency suitable to cause the transducer 150 to generate ultrasonic mechanical motions.

With continued reference to FIGS. 1A and 1B, the housing 130 includes a handle portion 131 having a compartment 132, which may house the power source 110, and a power source door 134 that secures the power source 110 within the compartment 132. In an aspect, the power source door 134 may be configured to form a water-tight seal between the interior and the exterior of the compartment 132.

The housing 130 also includes a cover 133, which houses the transducer 150 and an output device 180. The transducer 150 includes a generator assembly 152 and a transducer assembly 154, having a transducer body 156 and a locking portion 162 (FIG. 1B). The generator assembly 152 is electrically coupled to the transducer assembly 154 via a pair of contacts 158.

With reference to FIG. 1B, the transducer 150 is illustrated as being separate from the cover 133. When the transducer 150 is inserted into and assembled with the cover 133, the pair of contacts 158 is connected to the round groove of the transducer 150 so that the rotational movement of the transducer body 156 does not disrupt the connection between the transducer body 156 and the generator assembly 152. Thus, the transducer body 156 is capable of freely rotating within the housing 130.

The output device 180 outputs information about the ultrasonic surgical device 100 or, in various embodiments, a status of the mechanical coupling between the ultrasonic probe 190 and the transducer 150. In various embodiments, the output device 180 may also display a warning that the ultrasonic probe 190 is not adequately connected to the transducer 150. The method for detection of attachment of the ultrasonic probe is disclosed in U.S. Patent Application Publication No. 2016/0374711, the entire contents of which are hereby incorporated by reference into the present disclosure.

In another embodiment, the output device 180 may be a speaker configured to output audible tones denoting a proper or improper connection of the ultrasonic probe 190 to the transducer 150. In yet another embodiment, the output device 180 may include one or more light emitting devices, configured to emit lights of various duration, pulses, and colors indicating the status of the mechanical coupling between the ultrasonic probe 190 and the transducer 150.

The handle portion 131 further includes a trigger 136. When the trigger 136 is actuated, the power source 210 provides energy to the transducer 150 so that the transducer 150 is powered to generate ultrasonic mechanical motions of the ultrasonic probe 190. As the trigger 136 is released, the power supply to the transducer 150 is terminated.

The generator assembly 152 receives the DC power from the power source 210 and generates AC signals having a frequency greater than 20 kHz. The generator assembly 152 can generate signals having a frequency based on a desired mode of operation, which may be different from the resonant frequency of the transducer 150.

The transducer body 156 of the transducer assembly 154 receives the AC signal generated by the generator assembly 152 and generates ultrasonic mechanical motion within the ultrasonic probe 190 based on the amplitude and the frequency of the generated AC signal. The transducer body 156 includes a piezoelectric material, which converts the generated AC signal into ultrasonic mechanical motions.

The ultrasonic surgical device 100 also includes a spindle 170, which is coupled to the ultrasonic probe 190 and allows for rotation of the ultrasonic probe 190 about its longitudinal axis. The ultrasonic probe 190 is attached to the housing and is mechanically connected to the transducer 150 via the locking portion 162 such that as the spindle 170 is rotated about the longitudinal axis defined by the ultrasonic probe 190, the ultrasonic probe 190 and the transducer 150 are also rotated correspondingly without affecting the connection between the transducer 150 and the ultrasonic probe 190.

The ultrasonic probe 190 may include an end effector 194 suitable for sealing tissue by converting the longitudinal mechanical movements into heat. The ultrasonic probe 190 includes a waveguide 192, an end effector 194 extending from the waveguide 192, and a jaw member 196. The ultrasonic probe 190 is mechanically coupled to the transducer body 156 via the locking portion 162.

The jaw member 196 may be formed as a pivoting arm configured to grasp and/or clamp tissue between the jaw member 196 and the end effector 194. When the jaw member 196 and the end effector 194 grasp tissue and the end effector 194 conveys the ultrasonic mechanical motions, temperature of the grasped tissue between the end effector 194 and the jaw member 196 increases due to the ultrasonic mechanical motions. These motions in turn treat, e.g., cuts and/or seals, a vessel in the tissue. In accordance with an aspect of the present disclosure, and as discussed later herein, the end effector 194 may vibrate at a different velocity based on a size of a vessel to be sealed.

In accordance with aspects of the present disclosure, and as described in more detail later herein, by controlling the velocity of the mechanical motions of the end effector 194, the heating rate of the vessel may be controlled so that the vessel can be effectively sealed. For example, in various embodiments, the heating rate may be maintained to be a constant initial heating rate for an initial period of time until a particular amount of energy is supplied to the vessel, and then the heating rate may be changed to a heating rate curve until completion of the sealing of the vessel. The constant initial heating rate and/or the heating rate curve may vary depending on the size of the vessel. Further, the initial time period and the following time period until completion of the sealing may vary depending on the size of the vessel.

The illustrated embodiments of FIG. 1A and FIG. 1B are merely exemplary, and variations are contemplated to be within the scope of the present disclosure. For example, components need not be arranged or configured as illustrated in FIG. 1A and FIG. 1B, and may be arranged or configured in a different way while still performing the operations and/or functions described herein. For example, in various embodiments, the ultrasonic surgical device may not include an internal generator and/or may be connected to an external generator. The connection can couple electrosurgical power from the external generator to the ultrasonic surgical device and can convey measurements or feedback signals from the ultrasonic surgical device to the external generator. Such an external generator can perform some or all of the operations and functions described herein for the generator assembly 152. Other variations are contemplated to be within the scope of the present disclosure.

Figure 2:
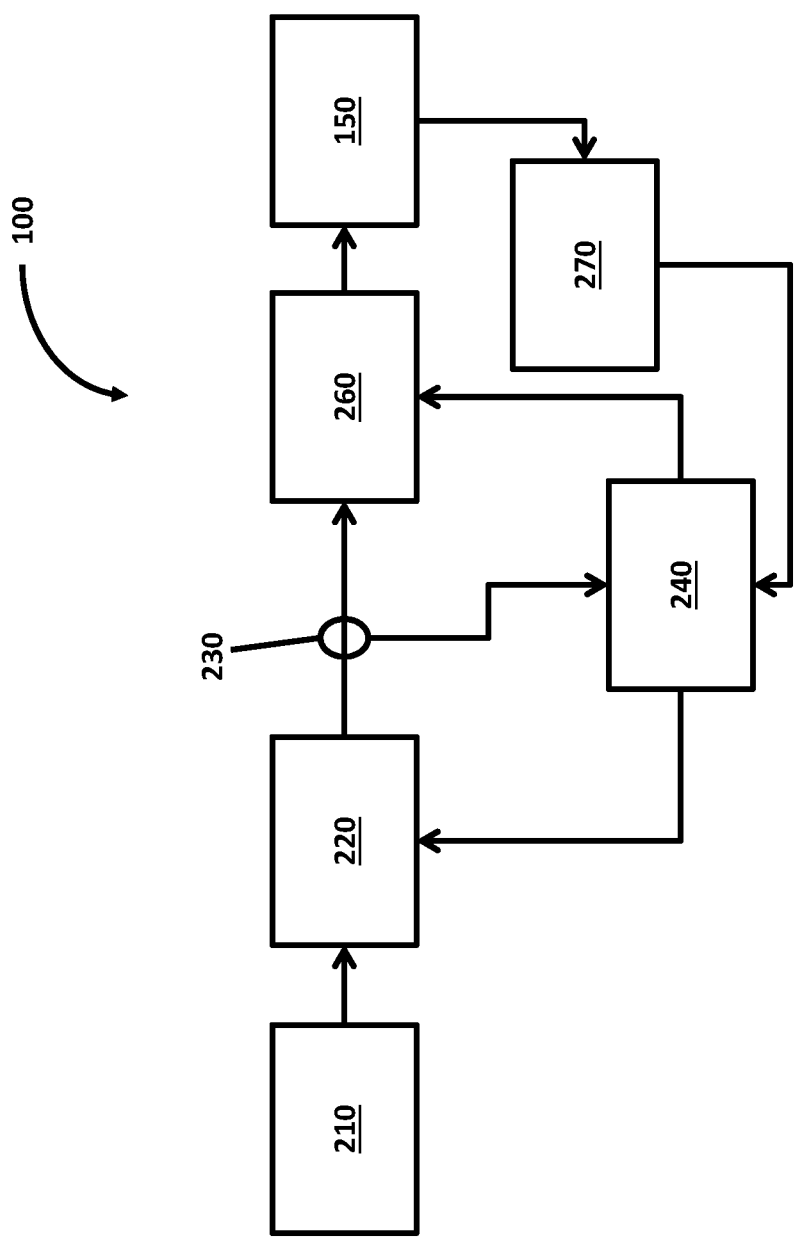
FIG. 2 is a functional block diagram of the ultrasonic surgical device of FIG. 1A in accordance with embodiments of the present disclosure.

FIG. 2 illustrates a block diagram of an ultrasonic surgical device or ultrasonic system in accordance with aspects of the present disclosure. As described above, the ultrasonic surgical device or system can estimate a size of a vessel to be sealed and provide electrical energy, which has a suitable power and frequency, to the transducer 150, which in turn provides ultrasonic mechanical motions to the end effector 194. An analog or digital pulse-width modulation (PWM) signal or delta-sigma signal may be used to regulate the ultrasonic mechanical motions. The ultrasonic surgical device or system includes the power source 210, a converter 220, a sensor 230, a controller 240, an inverter 260, the transducer 150, and a comparator 270. In various embodiments, some or all of the components can be included in an ultrasonic surgical device, such as a device 100 shown in FIGS. 1A and 1B. In various embodiments, some of the illustrated components are located in the ultrasonic surgical device and some of the components are located in an external generator.

The power source 210 provides DC power to the converter 220, which amplifies the voltage of the DC power so that ultrasonic surgical device 100 generates ultrasonic mechanical motions sufficiently large enough for treating the tissue. The sensor 230 then senses parameters related to the electrical energy flowing to the inverter 260. The sensed parameters may include sensed current waveforms and the sensed voltage waveforms of the electrical energy supplied to the inverter 260.

In various embodiments, the sensor 230 may include a temperature sensor at a distal portion of the end effector 194. The temperature sensor may sense a temperature of the distal portion of the end effector 194 and estimate a temperature of the vessel. The relationship between the temperature of the end effector and the vessel can be found in commonly assigned U.S. Pat. No. 10,130,412, the entire contents of which are incorporated by reference herein.

The sensor 230 may be a pressure sensor sensing a clamping force or pressure when the end effector 194 clamps the tissue containing the vessel. The sensor 230 may sense an aperture of the end effector 194. Further, the sensor 230 may be a tension sensor sensing a tension in the tissue. Measurements from theses sensors may be used to accurately measure the temperature of the vessel and other parameters for sealing the vessel.

The controller 240 receives the sensed parameters from the sensor 230, calculates various parameters (e.g., root-mean-square (RMS) or average voltage, current, power or impedance) based on the sensed parameters, and generates a control signal to control an amplitude of the electrical energy (e.g., amplitude of the RMS current, voltage, or power). In an aspect, the controller 240 may control a duty cycle of the converter 220. In various embodiments, a digital PWM signal or delta-sigma modulation signal may be used to control the duty cycle of the converter 220.

The inverter 260 receives the amplified voltage of the DC power from the converter 220. The inverter 260 is driven by output signals from the controller 240. In various embodiments, the inverter 260 may include an H-bridge structure to generate AC electrical energy having a suitable frequency to cause the transducer 150 to mechanically vibrate.

In various embodiments, the controller 240 may measure a velocity of the end effector 194 coupled to the transducer 150 and maintain a certain velocity of the end effector 194 to estimate a size of the vessel prior to a sealing process. Details for estimating the size of vessel may be found in commonly assigned U.S. patent application Ser. No. 16/391,635 filed on Apr. 23, 2019, entitled "Methods and Systems for Ultrasonic Vessel Sealing," the entire contents of which are hereby incorporated by reference herein. In summary, the comparator 270 receives a signal from the transducer 150, indicating a velocity of the end effector 194, and compares the velocity of the end effector 194 with a predetermined velocity set for estimating a size of the vessel.

After the size of vessel is estimated, the vessel can be characterized as a small vessel, e.g., the vessel is less than 5 millimeters (mm), or as a large vessel, e.g., the vessel is greater than or equal to 5 mm. Depending on the size of the vessel, the energy provided to seal the vessel can be controlled based on predetermined heating rates corresponding to the vessel size, which will be described in more detail in connection with FIG. 3.

The controller 240 may generate PWM control signals to drive the converter 220 and generate other control signals to drive the inverter 260. The controller 240 receives outputs from the comparator 270 and generates control signals for the inverter 260 in response to the output of the comparator 270. The inverter 260 then inverts the DC power to the AC power. In an aspect, a transformer (not shown) may be electrically coupled between the inverter 260 and the transducer 150 so that the transformer may increase the amplitude of the AC power to a desired level. In various embodiments, the controller 240 may generate other types of signals, such as delta-sigma modulation signals.

In an aspect, the sensor 230 is configured to sense voltage and current waveforms of the AC power supplied to the transducer 150 and transmit the sensor signals to the controller 240. The controller 240 may process the sensor signals and the output of the comparator 270 to control the velocity of the end effector 194, thereby achieving a desired heating rate of the vessel.

Figure 3:
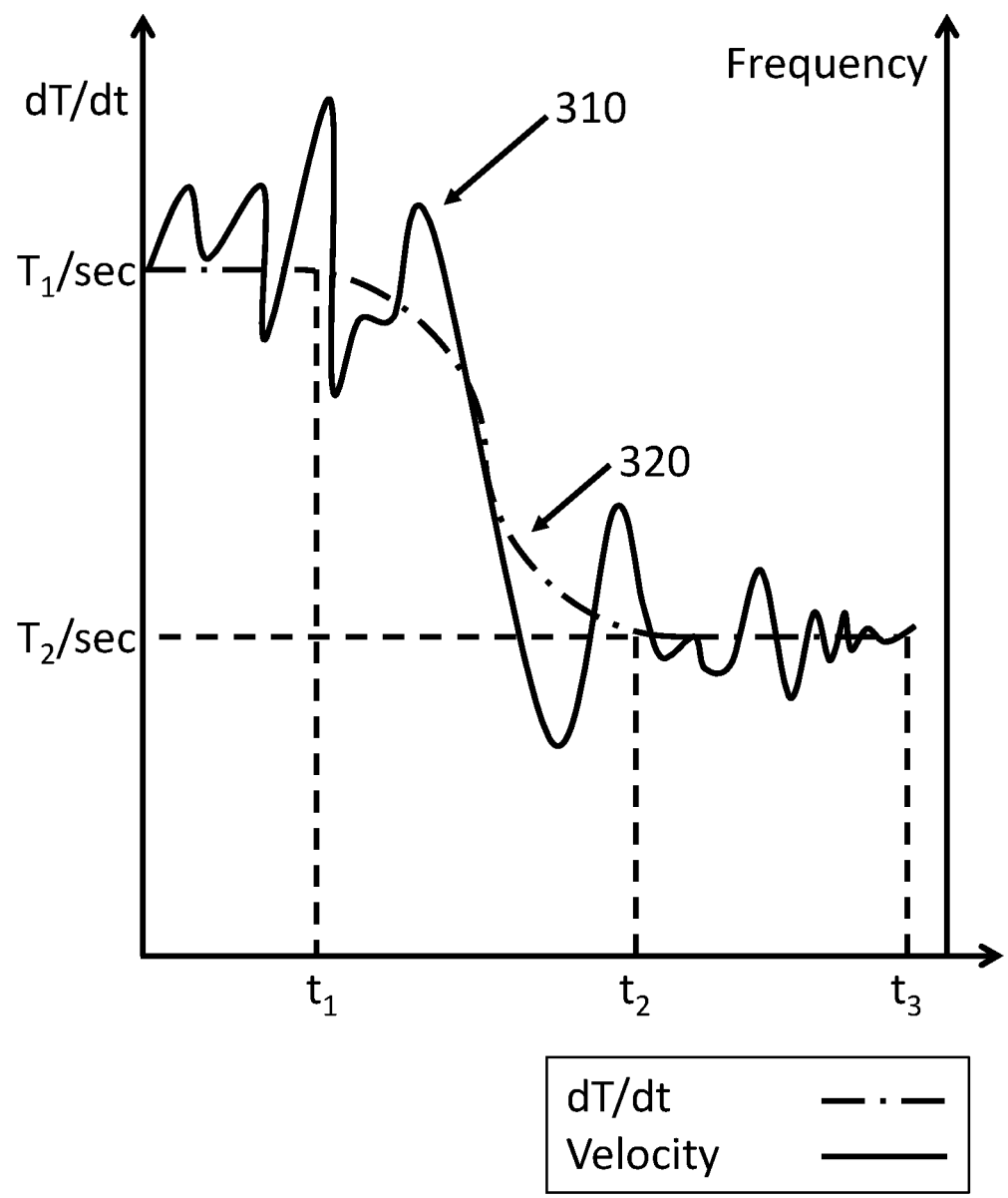
FIG. 3 is a graphical illustration showing a heating rate of vessel and frequency of a transducer over time in accordance with embodiments of the present disclosure.

In an aspect, the controller 240 may include a processor and a memory coupled to the processor. The processor may be any suitable processor (e.g., control circuit) adapted to perform operations, calculations, and/or set of instructions described in the present disclosure including, but not limited to, a hardware processor, a field programmable gate array (FPGA), a digital signal processor (DSP), a central processing unit (CPU), a microprocessor, and any combinations thereof. Those skilled in the art will appreciate that the processor may be substituted for by using any logic processor (e.g., control circuit) adapted to execute algorithms, calculations, and/or set of instructions described in this disclosure. The memory may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory FIG. 3 illustrates two graphical curves showing a target heating rate of a vessel over time 320 and a velocity of the end effector over time 310, in accordance with embodiments of the present disclosure. The horizontal axis represents time, the left vertical axis represents rate of change in temperature, corresponding to the heating rate curve 320, and the right vertical axis represents velocity, corresponding to the velocity of the end effector 310. The frequency of the transducer may be controlled separately from the velocity of the end effector, which reflects the amount of displacement of the end effector in motion. Accordingly, when the ultrasonic transducer is driven at a resonance frequency, the velocity of the end effector can still be adjusted to achieve different heating rates of a vessel.

As mentioned above herein, and in accordance with aspects of the present disclosure, when the end effector initially grasps a vessel, the ultrasonic surgical device may estimate a size of the vessel. Based on the size of the vessel, the ultrasonic surgical device supplies electric energy to the transducer based on a predetermined heating rate curve corresponding to the vessel size. FIG. 3 illustrates one example of a heating rate curve 320 for a vessel size or a range of vessel sizes, such as 5 mm-7 mm.

Curve 310 of FIG. 3 shows the velocity of the end effector over time and curve 320 shows the predetermined heating rate curve for heating the vessel over time. In accordance with aspects of the present disclosure, the velocity of the end effector 194 can be controlled to achieve a tissue heating rate that tracks the predetermined heating rate curve 320. In various embodiments, the tissue heating rate can be estimated by detecting the rate of change of the resonant frequency of the transducer over time. As mentioned above, temperature affects the resonant frequency of the transducer such that there is a relationship between temperature and resonant frequency of the transducer. Accordingly, monitoring the rate of change of the resonant frequency can provide an estimate of the heating rate of the tissue.

With continuing reference to FIG. 3, the velocity of the end effector 194 may be controlled to maintain a predetermined initial heating rate, $T_1$/sec, until $t_1$. During this period until $t_1$, a predetermined amount of electrical energy is supplied by an internal generator or an external generator. For example, the predetermined amount of energy supplied until $t_1$ may be 20 J for a 1 mm vessel and 40 J for a 7 mm vessel. The time $t_1$ may vary depending on the size of the vessel. For example, $t_1$ may be 0.5 seconds for a 1 mm vessel and 3 seconds for a 7 mm vessel. These predetermined amounts of energy and times of $t_1$ are provided for showing examples only, and may vary in different embodiments. As described earlier in connection with FIG. 2, the amount of energy supplied can be determined using sensor 230.

Between times $t_1$ and $t_2$, the velocity of the end effector is controlled to change the heating rate of the vessel based on a predetermined heating rate curve. In the illustrated embodiment, the predetermined heating rate curve decreases from the initial heating rate $T_1$/sec down to a lower heating rate $T_2$/sec. After $t_2$, the velocity of the end effector is further controlled based on a lower heating rate, $T_2$/sec, of the vessel. The sealing of the vessel may be complete at $t_3$.

In various embodiments, the total amount of energy until completion of sealing the vessel may be predetermined depending on the size of the vessel. Further, the total amount of energy may be divided into two or more amounts of energy. As an example, a first amount of energy can be provided until $t_1$, a second amount of energy can be provided during the transition between $t_1$ and $t_2$, and a third amount of energy can be provided from $t_2$ to $t_3$, until completion of the sealing.

In another embodiment, $t_1$, $t_2$, and $t_3$ may be predetermined depending on the size of the vessel.

Figure 4:
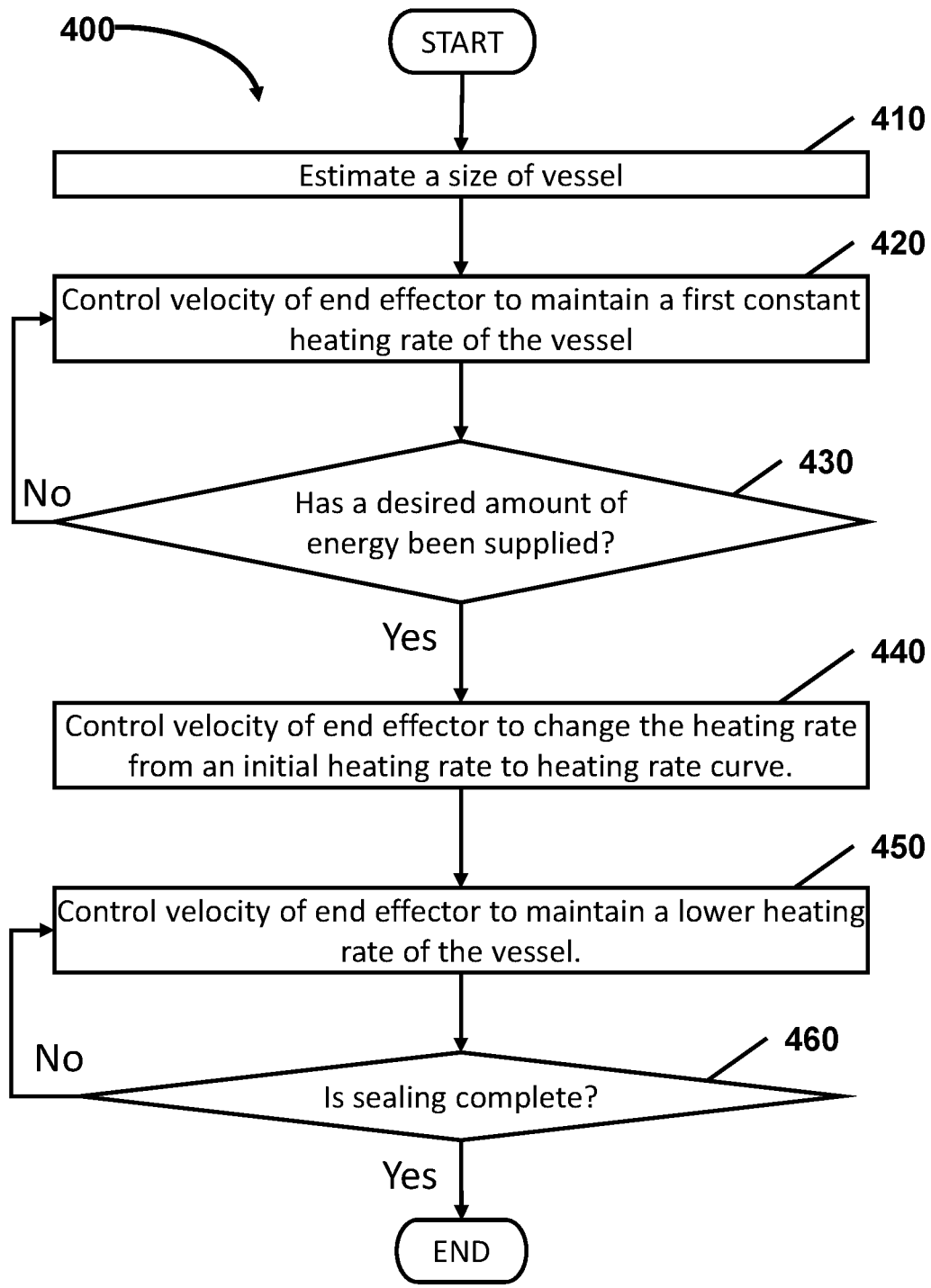
FIG. 4 is a flow chart illustrating a method for controlling a heating rate to seal a vessel based on a size of the vessel in accordance with embodiments of the present disclosure.

FIG. 4 shows a flow chart illustrating a method 400 for sealing a vessel depending on the size of the vessel, in accordance with embodiments of the present disclosure. The method 400 includes at least two phases, a phase for estimating a size of the vessel and a phase for properly sealing the vessel based on the estimated size of the vessel.

In step 410, the size of the vessel is estimated. As described above, the technique for the vessel size estimation can be found in commonly assigned U.S. Provisional Patent Application No. 62/678,724, filed on May 31, 2018, and entitled "Methods and Systems for Ultrasonic Vessel Sealing," which is hereby incorporated by reference herein in its entirety.

Based on the estimated size of the vessel, the velocity of the end effector may be controlled based on maintaining the heating rate of the vessel to track a predetermined initial heating rate in step 420. While the vessel is heated, the characteristics of the vessel may change. For example, the impedance of the vessel may change. Thus, the velocity of the end effector may be controlled to accommodate changes in characteristics of the vessel to maintain the heating rate of the vessel. The control of velocity of the end effector is shown in FIG. 3.

In step 430, it is determined whether or not a predetermined amount of energy should have been supplied by a generator to the vessel. The predetermined amount of energy may depend on the size of the vessel. For example, large vessels may need more energy than smaller vessels for a proper sealing of the vessel. Thus, the amount of energy to be supplied may be predetermined corresponding to the size of the vessel. For example, the ultrasonic surgical device or system may store in a memory a lookup table that correlates the size of the vessel with a predetermined amount of energy to be supplied by the generator.

The ultrasonic surgical device continues to supply energy until the predetermined amount of energy is supplied by the generator to the vessel. When it is determined that the predetermined amount of energy is supplied by the generator to the vessel, in step 430, the heating rate is changed from the predetermined initial heating rate to a predetermined heating rate curve that decreases from the predetermined initial heating rate, in step 440. This step is performed by controlling the velocity of the end effector based on the predetermined heating rate curve.

In step 450, the heating rate of the vessel is maintained to a lower heating rate, and in step 460, it is determined whether or not the sealing of the vessel is complete. Thus, in various embodiments, the lower heating rate is maintained until the sealing of the vessel is complete.

Since other modifications and changes may be made to fit particular operating requirements and environments, it is to be understood by person skilled in the art that the present disclosure is not limited to the illustrative examples described herein and may cover various other changes and modifications which do not depart from the spirit or scope of this disclosure. The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described operations, methods, programs, algorithms or codes may be converted to, or expressed in, a programming language or computer program. The terms "programming language," and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "set of instructions," "programming language," and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other metalanguages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A method for sealing a vessel comprising:
   supplying electrical energy to an ultrasonic surgical instrument having an end effector and a transducer coupled to the end effector, when the end effector is grasping the vessel;
   sensing parameters of the vessel when the end effector achieves a predetermined velocity;
   estimating a size of the vessel based on the sensed parameters;
   controlling the electrical energy based on maintaining a predetermined initial heating rate of heating the vessel until a predetermined amount of energy corresponding to the estimated size of the vessel has been delivered; and
   controlling the electrical energy to seal the vessel based on a predetermined heating rate curve of heating the vessel after the predetermined amount of energy corresponding to the estimated size of the vessel has been delivered.

2. The method according to claim 1, wherein the predetermined heating rate curve decreases from the predetermined initial heating rate.

3. The method according to claim 1, wherein sensing parameters of the vessel includes sensing an impedance of the vessel.

4. The method according to claim 1, wherein controlling the electrical energy based on maintaining the predetermined initial heating rate of heating the vessel includes controlling the electrical energy based on maintaining the predetermined heating rate of heating the vessel until 20 joules of energy have been delivered, when the estimated size of the vessel is less than 5 millimeters.

5. The method according to claim 1, wherein controlling the electrical energy based on maintaining the predetermined initial heating rate of heating the vessel includes controlling the electrical energy based on maintaining the predetermined initial heating rate of heating the vessel until 40 joules of energy have been delivered, when the estimated size of the vessel is greater than or equal to 5 millimeters.

6. The method according to claim 1, wherein controlling the electrical energy based on the predetermined heating rate curve of heating the vessel includes halting the electrical energy after a predetermined duration of time.

7. The method according to claim 1, wherein controlling the electrical energy based on maintaining the predetermined initial heating rate of heating the vessel includes detecting a rate of change of a resonant frequency of the transducer over time.

8. The method according to claim 7, wherein controlling the electrical energy based on maintaining the predetermined initial heating rate of heating the vessel includes controlling an amplitude of the electrical energy based on the detected rate of change of the resonant frequency over time.

9. The method according to claim 1, wherein controlling the electrical energy based on the predetermined heating rate curve of heating the vessel includes detecting a rate of change of a resonant frequency of the transducer over time.

10. The method according to claim 9, wherein controlling the electrical energy based on the predetermined heating rate curve of heating the vessel includes controlling an amplitude of the electrical energy based on the detected rate of change of the resonant frequency over time.

11. An ultrasonic surgical system comprising:
    a transducer;
    an end effector coupled to the transducer and configured to grasp and seal a vessel;
    a power source configured to supply electrical energy for the transducer;
    a sensor configured to sense parameters of the vessel when the end effector achieves a predetermined velocity; and
    a controller configured to:
    estimate a size of the vessel based on the sensed parameters;

control the electrical energy based on maintaining a predetermined initial heating rate of heating the vessel until a predetermined amount of energy corresponding to the estimated size of the vessel has been delivered; and control the electrical energy based on a predetermined heating rate curve of heating the vessel after the predetermined amount of energy corresponding to the estimated size of the vessel has been delivered.

12. The ultrasonic surgical system according to claim 11, wherein the predetermined heating rate curve decreases from the predetermined initial heating rate.

13. The ultrasonic surgical system according to claim 11, wherein the sensed parameters include an impedance of the vessel.

14. The ultrasonic surgical system according to claim 11, wherein the predetermined amount of energy is 20 joules when the estimated size of the vessel is less than 5 millimeters.

15. The ultrasonic surgical system according to claim 11, wherein the predetermined amount of energy is 40 joules when the estimated size of the vessel is greater than or equal to 5 millimeters.

16. The ultrasonic surgical system according to claim 11, wherein the controller is configured, in controlling the electrical energy based on the predetermined heating rate curve of heating the vessel, to halt the electrical energy after a predetermined duration of time.

17. The ultrasonic surgical system according to claim 11, wherein the controller is configured, in controlling the electrical energy based on maintaining the predetermined initial heating rate of heating the vessel, to detect a rate of change of a resonant frequency of the transducer over time.

18. The ultrasonic surgical system according to claim 17, wherein the controller is configured, in controlling the electrical energy based on maintaining the predetermined initial heating rate of heating the vessel, to control an amplitude of the electrical energy based on the detected rate of change of the resonant frequency over time.

19. The ultrasonic surgical system according to claim 11, wherein the controller is configured, in controlling the electrical energy based on the predetermined heating rate curve of heating the vessel, to:
 detect a rate of change of a resonant frequency of the transducer over time, and
 control an amplitude of the electrical energy based on the detected rate of change of the resonant frequency over time.

20. A nontransitory storage medium storing instructions that, when executed by a processor, cause the processor to perform a method for sealing a vessel, the method comprising:
 supplying electrical energy to an ultrasonic surgical instrument having an end effector and a transducer coupled to the end effector, when the end effector is grasping the vessel;
 sensing parameters of the vessel when the end effector achieves a predetermined velocity;
 estimating a size of the vessel based on the sensed parameters;
 controlling the electrical energy based on maintaining a predetermined initial heating rate of heating the vessel until a predetermined amount of energy corresponding to the estimated size of the vessel has been delivered; and
 controlling the electrical energy to seal the vessel based on a predetermined heating rate curve of heating the vessel after the predetermined amount of energy corresponding to the estimated size of the vessel has been delivered.

* * * * *